(12) United States Patent
Chung

(10) Patent No.: US 12,178,547 B2
(45) Date of Patent: Dec. 31, 2024

(54) ALL-IN-ONE BATTERY-POWERED HANDHELD OCT SYSTEM FOR POINT-OF-CARE DIAGNOSTICS

(71) Applicant: PHILOPHOS, INC., Seongnam-si (KR)

(72) Inventor: Jung-Ho Chung, Yongin-si (KR)

(73) Assignee: PHILOPHOS, INC., Seongnam-si (KR)

( * ) Notice: Subject to any disclaimer, the term of this patent is extended or adjusted under 35 U.S.C. 154(b) by 803 days.

(21) Appl. No.: 17/110,947

(22) Filed: Dec. 3, 2020

(65) Prior Publication Data

US 2021/0085185 A1  Mar. 25, 2021

Related U.S. Application Data

(63) Continuation of application No. PCT/KR2019/006756, filed on Jun. 4, 2019.

(30) Foreign Application Priority Data

Jun. 5, 2018 (KR) .................. 10-2018-0064957
Aug. 27, 2018 (KR) .................. 10-2018-0100659

(51) Int. Cl.
*A61B 5/00* (2006.01)
*A61B 1/00* (2006.01)
(Continued)

(52) U.S. Cl.
CPC ........ *A61B 5/0066* (2013.01); *A61B 1/00013* (2013.01); *A61B 1/00027* (2013.01);
(Continued)

(58) Field of Classification Search
CPC .............. A61B 5/0066; A61B 1/00013; A61B 1/00027; A61B 1/00045; A61B 1/0661;
(Continued)

(56) References Cited

U.S. PATENT DOCUMENTS

2007/0278384 A1* 12/2007 Heppell ................. H05B 1/025
250/205
2014/0121507 A1* 5/2014 Nau, Jr. ............. A61B 18/1445
606/207

(Continued)

FOREIGN PATENT DOCUMENTS

JP    H01234812 A    9/1989
JP    2001046321 A    2/2001
(Continued)

OTHER PUBLICATIONS

Office Action issued on Korean Application No. KR 10-2021-0003410 dated Mar. 17, 2021.
(Continued)

*Primary Examiner* — Aaron B Fairchild
(74) *Attorney, Agent, or Firm* — Dinsmore & Shohl LLP; Yongsok Choi, Esq.

(57) ABSTRACT

An all-in-one handheld optical coherence tomography (OCT) device having a built-in battery according to an embodiment of the present disclosure includes an optical unit provided in a region inside an all-in-one housing, a circuit unit provided in another region inside the all-in-one housing and configured to perform signal processing of the optical unit and management of power, and a power supply unit configured to supply power to the optical unit and the circuit unit and mounted inside the all-in-one housing.

15 Claims, 3 Drawing Sheets

(51) Int. Cl.
  *A61B 1/06* (2006.01)
  *A61B 1/07* (2006.01)
(52) U.S. Cl.
  CPC ........ *A61B 1/00045* (2013.01); *A61B 1/0661* (2013.01); *A61B 1/07* (2013.01); *A61B 1/00009* (2013.01)
(58) Field of Classification Search
  CPC .................. A61B 1/07; A61B 1/00009; A61B 2560/0431; A61B 1/00163
  See application file for complete search history.

(56) References Cited

U.S. PATENT DOCUMENTS

| | | | |
|---|---|---|---|
| 2014/0121508 A1 | 5/2014 | Latimer et al. | |
| 2014/0163361 A1* | 6/2014 | Stigall | A61B 8/12 600/463 |
| 2014/0204337 A1 | 7/2014 | Kulkarni et al. | |
| 2014/0309526 A1 | 10/2014 | Margallo Balbás et al. | |
| 2016/0223754 A1* | 8/2016 | Yamazaki | G03B 15/03 |
| 2016/0238371 A1* | 8/2016 | Lloret Soler | A61B 5/0066 |
| 2017/0042422 A1* | 2/2017 | Sakai | A61B 3/0016 |
| 2018/0045501 A1 | 2/2018 | Elmaanaoui | |
| 2019/0021601 A1* | 1/2019 | Subhash | A61B 5/0088 |

FOREIGN PATENT DOCUMENTS

| | | |
|---|---|---|
| JP | 2004113780 A | 4/2004 |
| JP | 2004333639 A | 11/2004 |
| JP | 2009510445 A | 3/2009 |
| JP | 2011240155 A | 12/2011 |
| JP | 2014504520 A | 2/2014 |
| JP | 5788874 B2 | 10/2015 |
| JP | 2016172041 A | 9/2016 |
| JP | 2017506947 A | 3/2017 |
| JP | 2018512210 A | 5/2018 |
| KR | 1020080081565 A | 9/2008 |
| KR | 101355671 B1 | 1/2014 |
| KR | 101746353 B1 | 6/2017 |
| KR | 101765824 B1 | 8/2017 |
| KR | 101853101 B1 | 4/2018 |
| WO | 2016019235 A1 | 2/2016 |
| WO | 2018119077 A1 | 6/2018 |

OTHER PUBLICATIONS

European Search Report of EP Application No. 19814719.1 dated Jan. 28, 2022.
Office Action issued on Japanese Application No. 2021-517175 dated Jan. 18, 2022.
European Commission: "EU GPP Criteria for Electrical and Electronic Equipment used in the Health Care Sector (Health Care EEE)", Apr. 19, 2015.
International Search Report of PCT/KR2019/006756 dated Sep. 3, 2019.
European Examination Report of EP Application No. 19814719.1 dated Dec. 20, 2023.

* cited by examiner

ALL-IN-ONE BATTERY-POWERED HANDHELD OCT SYSTEM FOR POINT-OF-CARE DIAGNOSTICS

CROSS-REFERENCE TO RELATED APPLICATION

This application is a continuation of International Application No. PCT/KR2019/006756 filed on Jun. 4, 2019, which claims priority to Korean Patent Application No. 10-2018-0064957 filed on Jun. 5, 2018 and Korean Patent Application No. 10-2018-0100659 filed on Aug. 27, 2018, the entire contents of which are herein incorporated by reference.

TECHNICAL FIELD

The present disclosure relates to a technology for implementing an all-in-one battery-powered handheld optical coherence tomography (OCT) system for Point-of-Care (POC) diagnostics.

BACKGROUND

OCT is an advanced medical diagnostic technology that enables the inside of a biological tissue to be observed and has been used in the fields of ophthalmology, cardiovascular medicine and the like. An OCT system can be implemented by time domain, spectral domain and swept source. Particularly, a spectral domain OCT system ensures a certain level of performance and requires less manufacturing cost and thus has received a lot of attention.

In general, an OCT system is composed of a probe and a main body. The probe functions to transmit light emitted from a light source to a biological tissue to be observed and transmit light backscattered from the tissue to the main body, and includes a sample optical path sub-system comprised of optical components such as a beam scanner configured to change the direction of light within a predetermined range, a lens, a mirror and the like, and a mount to fix the probe on the biological tissue. The main body includes a light source, a driver for the light source, a light separator such as a directional coupler or a beam splitter configured to divide a beam of light emitted from the light source into two beams in two different directions, a reference optical path sub-system configured to generate an optical path matched with light transmitted toward the probe, a detector configured to detect interference components between light returning from the reference optical path sub-system and light returning from the sample optical path sub-system of the probe, and the like. In some cases, such sub-systems as the light separator, the reference optical path sub-system, and so on, may be located in the probe.

A detected optical signal which has been converted into an electrical signal generates an OCT signal through signal processing. This may be performed by means of a signal processing unit such as a microprocessor unit (MCU) included in the main body. Otherwise, the OCT system may serve as a peripheral device of a general PC and the detected signal may be transmitted to the PC through a connector, and the PC may perform signal processing.

FIG. 1 illustrates an example of the configuration of a conventional OCT system.

Referring to FIG. 1, an OCT system includes a main body, a PC and a probe, and may be configured into two representative types as shown in the drawing.

The conventional OCT system may be configured into a cart-structure and can make limited movements within a restricted space, or may be configured into a fixed desktop structure. In other words, the main body and the PC are fixed to the floor and only the probe can make restricted movements to approach a biological tissue of a testee.

In this usage environment, a diagnosis can be made only when a testee or a patient visits a predetermined place where the device is located, which greatly limits the availability of OCT.

If there is an OCT device that can be readily used like a stethoscope when a doctor interviews a patient and can also be used in mountainous areas or islands with low health service access, the availability of the OCT can be greatly improved.

Another factor limiting the availability of the OCT is high installation cost. An OCT device configured into a cart or desktop structure as described above costs about one hundred million one. Therefore, it is not easy for medical facilities, such as primary or secondary doctor's offices, except large hospitals, to equip those OCT devices.

In general, as an optical component such as a lens gets smaller in size, the price thereof drops, and if the OCT device can be compact and all-in-one by removing optical components for signal transmission between the main body and the probe, the price of the entire OCT system can be reduced and OCT diagnostics can give benefits to more people.

SUMMARY

Problems to be Solved by the Invention

The present disclosure provides an all-in-one (single-body) OCT device with maximized portability to increase the utility value of OCT technology.

Means for Solving the Problems

To solve the above-described problem, an all-in-one handheld optical coherence tomography (OCT) device having a built-in battery according to an embodiment of the present disclosure includes: an optical unit provided in a region inside an all-in-one housing; a circuit unit provided in another region inside the all-in-one housing and configured to perform signal processing of the optical unit and management; and a power supply unit equipped with a built-in battery, configured to supply power to the optical unit and the circuit unit and mounted inside the all-in-one housing.

Further, the all-in-one housing may have a shape capable of housing the optical unit, the circuit unit and the power supply unit and, on its outside, include grip finger grooves, which enables a user to grasp the all-in-one housing.

Furthermore, a manipulation unit, which is connected to the circuit unit and through which the OCT device is manipulated, may be provided on the outside of the all-in-one housing.

Moreover, the circuit unit may be formed into a planar shape elongated in one direction, and the optical unit may be arranged so that a light emission assembly configured to emit light passing through the optical unit may be arranged on one side of the all-in-one housing and a light source unit configured to supply a light source to the optical unit may be arranged on the other side. The light source unit may be connected to the circuit unit with at least one electric wire, and the circuit unit may be located to be superposed onto the optical unit within an inner space of the all-in-one housing.

Besides, the light source unit, a detector, a reference optical path sub-system, a sample optical path sub-system and a light separator may be connected to each other and may form an interferometer, and the sample optical path sub-system may be provided in a direction from the light emission assembly toward a biological tissue to be examined.

Further, the light emission assembly may be elongated to a predetermined length in order to be used as an endoscope or laparoscope.

Furthermore, the circuit unit may include a light source controller, a light emission controller, a detection circuit unit, a central processing unit, a power supply controller, a communication processing unit and a user interface (UI) controller unit.

Moreover, the central processing unit may control the light source controller to perform ON/OFF control of the light source and adjust an output level of the light source depending on predetermined situations.

Besides, if an OCT system is not operated for a predetermined period of time, the OCT system may be put into a standby mode in which the OCT system is paused, and the parameters set while the user has used the OCT system right before the standby mode may be backed up in order for the OCT system to respond to the user's manipulation.

Further, if the OCT system is maintained in the standby mode for a predetermined period of time, the power supply controller may put the OCT system into a mode for system shutdown.

Furthermore, the light source may be turned on for a predetermined period of warm-up time in advance before a measurement signal is initiated and automatically turned off after the measurement signal is ended, and the warm-up time refers to the amount of time required for the output level of the light source to converge into a value within a predetermined range.

Moreover, while the light source controller controls the light source to turn on and warm up, the light emission controller may adjust the focus on a measurement site and input signals for beam scanning.

Besides, if the light source controller detects that a temperature of the light source is higher than a predetermined temperature or an output level of the light source is lower than a predetermined value, the light source controller may adjust a current supplied to the light source.

Further, if the temperature of the light source is higher than another predetermined temperature, the light source controller may give a warning alarm or turn off the light source.

Furthermore, optical fibers between the light separator, the reference optical path sub-system, the sample optical path sub-system, the light source and the detector may be formed to less than a predetermined length and connected by splicing without connectors.

Moreover, the light source controller of the circuit unit and the light source unit including the light source of the optical unit, may have a rugged surface structure in order to enhance heat conduction of internal chips.

Also, a method of displaying OCT data acquired by an all-in-one handheld OCT device having a built-in battery in connection with a user terminal includes: a process of generating OCT data and transmitting the OCT data from the battery-embedded all-in-one handheld OCT device to the user terminal; and a process of mapping the testee's information previously inserted by the user, storing the OCT data, and playing the OCT data through a display module of the user terminal at the user terminal that has received OCT data, and the battery-embedded all-in-one handheld OCT device includes: an optical unit provided in a region inside the all-in-one housing; a circuit unit provided in another region inside the all-in-one housing and configured to perform signal processing of the optical unit and device managing; and a power supply unit equipped with the built-in battery, configured to supply power to the optical unit and the circuit unit and mounted inside the all-in-one housing.

Effects of the Invention

According to an embodiment of the present disclosure, an all-in-one (single-body) OCT device with maximized portability is proposed to increase the utility value of the OCT technology.

According to the present disclosure, an all-in-one OCT system that can be used in a handheld or mobile environment can lower installation cost and reduce limitations in spatial access, which results in further spread of the benefits of this technology. Also, if a new device applicable to dermatology and gynecology as well as cardiovascular medicine comes out based on the present disclosure, the utility of this technology can be further expanded.

DETAILED DESCRIPTION

Figure 1:
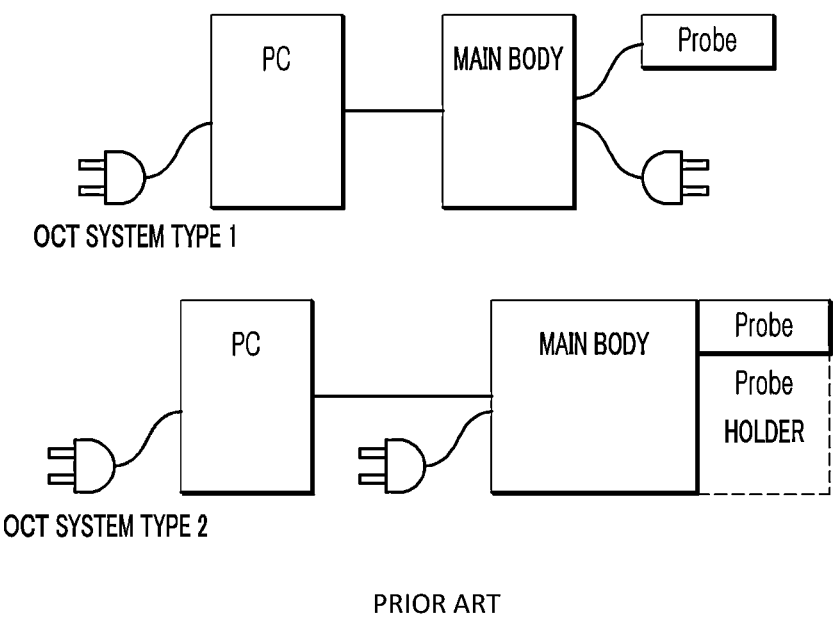
FIG. 1 illustrates an example of the configuration of a conventional OCT system.

Hereafter, embodiments will be described in detail with reference to the accompanying drawings so that the present disclosure may be readily implemented by a person with general knowledge in the art. However, it is to be noted that the present disclosure is not limited to the embodiment described here but can be embodied in other various ways. In the drawings, parts irrelevant to the description are omitted for the simplicity of explanation, and like reference numerals denote like parts throughout the whole document.

Throughout the whole document, the term "connected to" or "coupled to" that is used to designate a connection or coupling of one element to another element includes both a case that an element is "directly connected or coupled to" another element and a case that an element is "electronically connected or coupled to" another element via the other element. Further, it is to be understood that the term "comprises or includes" and/or "comprising or including" used in the document means that one or more other components, steps, operations and/or existence or addition of elements are not excluded but may be included in addition to the described components, steps, operation and/or elements unless the context dictates otherwise and is not intended to preclude the possibility that one or more other features, numbers, steps, operations, components, parts, or combinations thereof may exist or may be added.

Throughout the whole document, the term "unit" includes a unit implemented by hardware, a unit implemented by software, and a unit implemented by both of them. Also, one unit may be implemented by two or more pieces of hardware, and two or more units may be implemented by one piece of hardware. However, "the unit" is not limited to the software or the hardware, and "the unit" may be configured to be saved in an addressable storage medium or to invoke one or more processors. Accordingly, "the unit" may include, for example, such elements as software elements, object-oriented software elements, class elements, task elements, and the like, processes, functions, attributes, procedures, sub-routines, segments of program codes, drivers, firmware, micro codes, circuits, data, database, data structures, tables, arrays, variables and the like. The components and functions provided by "a unit" can be combined with each other or can be divided up into additional components and "units". Further, the components and "the units" may be configured to run one or more CPUs in a device or a secure multimedia card.

The following exemplary embodiments are provided only for understanding of the present disclosure but not intended to limit the scope of the right of the present disclosure. Therefore, the inventions that perform the same functions in the same scope as the present disclosure are also included in the scope of the right of the present disclosure.

Figure 2:
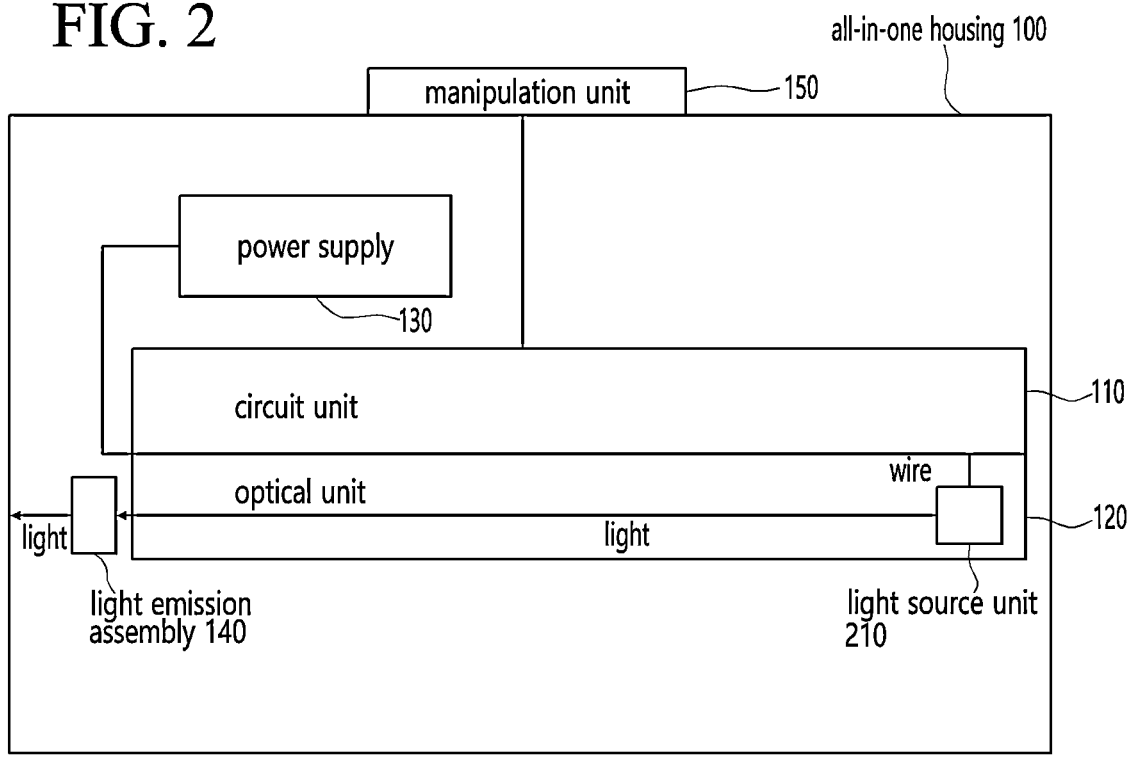
FIG. 2 illustrates the configuration of a handheld OCT device according to an embodiment of the present disclosure.

FIG. 2 illustrates the configuration of a handheld OCT device 1 according to an embodiment of the present disclosure.

Referring to FIG. 2, the handheld OCT device 1 may include a circuit unit 110, an optical unit 120 and a power supply unit 130.

In the OCT device 1, the circuit unit 110, the optical unit 120 and the power supply unit 130 are configured as a single body and housed in an all-in-one housing 100 so as to be handheld. The all-in-one-housing 100 has grip finger grooves, which enable a user to grasp the handheld OCT device 1, on its outside. The all-in-one housing 100 is implemented similar in shape and size to a TV remote controller, and, thus, the portability can be maximized.

Also, a manipulation unit 150 through which the OCT device 1 is manipulated is provided around the finger grooves of the all-in-one housing 100. The manipulation unit 150 may be implemented as a push or toggle button or may be implemented on a small-sized touch screen.

Herein, as an additional embodiment, the OCT device 1 may further include a small-sized display screen for displaying an operation status of the handheld OCT device 1 or acquired information, and the small-sized display screen may be connected to a UI controller unit included in the circuit unit 110.

The handheld OCT device 1 includes the optical unit 120 provided in a region inside the all-in-one housing 100 and the circuit unit 110 that is provided in another region inside the all-in-one housing 100 and that is configured to perform signal processing of the optical unit 120 and power management. Further, the power supply unit 130 configured to supply power to the circuit unit 110 and the optical unit 120 is mounted in another region inside the all-in-one housing 100.

More specifically, the circuit unit 110 is formed into a planar shape elongated in one direction except portions closely connected to the optical unit 120. If the optical unit 120 is implemented mainly as a geometric optical system, the optical unit 120 has a cuboid shape with a shorter length and a greater thickness than the circuit unit 110.

Therefore, a light emission assembly 140 configured to emit light passing through the optical unit 120 may be arranged on one side of the all-in-one housing 100 and a light source unit 210 configured to supply a light source to the optical unit 120 may be arranged on the other side. That is, when the optical unit 120 is arranged on one side within the all-in-one housing 100, the circuit unit 110 may occupy an inner space of the all-in-one housing 100 in a plane and may be superposed onto the optical unit 120 within the inner space of the all-in-one housing 100, and the power supply unit 130 may be arranged in the remaining space. Here, the light source unit 210 may be connected to the circuit unit 110 with electric wires.

Here, a heat dissipation plate having a rugged surface for reducing temperature increase caused by application of power to the light source may be provided inside the light source unit 210, and each module forming the circuit unit 110 or the optical unit 120 may have a rugged surface structure in order to enhance heat conduction.

The circuit unit 110 is configured as circuit boards and functions to control the entire handheld OCT device 1, and details thereof will be described below with reference to FIG. 4.

The optical unit 120 is comprised of optical components such as the light source unit 210, an interferometer, a detector and a beam scanner. Some of these components perform the function of the probe of a conventional OCT device. Details of the optical unit 120 will be described below with reference to FIG. 3.

The power supply unit 130 plays the role to supply power to each part of the handheld OCT device 1 and may be implemented in the form of a battery so that the handheld OCT device 1 can be operated by using a built-in power supply without using an external power supply. Thus, the handheld or mobile OCT device can be implemented without a wired connection to a separate external device.

Therefore, if power in the power supply is exhausted, a battery may be replaced or a built-in battery may be charged from an external power source through a charging slot (or a structure of cradle mount).

The handheld OCT device 1 may further include an additional structure such as an OCT holder, and additional accessories for the handheld OCT device 1 do not limit the scope of the present disclosure.

Here, the OCT holder may be used when it is not easy for a user to make a measurement due to hand vibration or when a testee himself/herself makes a measurement without a tester. Here, the OCT holder may be connected to the handheld OCT device 1 in a wireless or wired manner as in a selfie stick of a conventional smart device, and the commands to operate the handheld OCT device 1 may be given through the OCT holder. For example, the start and end of imaging can be manipulated and the position of the handheld OCT device 1 coupled to the OCT holder can be moved to accurately align the light emission assembly 140 of the OCT device to a measurement site. Besides, the battery of the handheld OCT device 1 may be charged by being coupled to the OCT holder, or the handheld OCT device 1 may be equipped with a joint structure that enables the handheld OCT device 1 to be accurately located on a measurement site of a testee.

Further, the handheld OCT device 1 is supposed to be used while the user is holding it, and, thus, the handheld OCT device 1 needs to be designed so that it withstands drops or impacts and implemented to facilitate heat dissipation. Here, in order to effectively dissipate heat from the inside of the device, air flow holes may be formed in one surface of the all-in-one housing 100 so that air inside the device can circulate to the outside, or a cooling fan may be provided so that the temperature inside the device can be lowered by operating the cooling fan.

In another embodiment, contamination may occur in the light emission assembly 140 due to frequent measurements with the handheld OCT device 1. Therefore, a replaceable cover may be provided, and the cover contaminated after used for a predetermined period of time can be replaced.

In yet another embodiment, a display panel connected to the circuit unit 110 may be provided on the outside of the all-in-one housing 100 of the handheld OCT device 1. The display panel may guide instructions to the user using the handheld OCT device 1, indicate operation states, or play OCT images. If the display panel is equipped with the touch screen as an input method, the display panel may be connected to a user interface (UI) controller unit 370 and may function as an input device corresponding to the manipulation unit.

Figure 3:
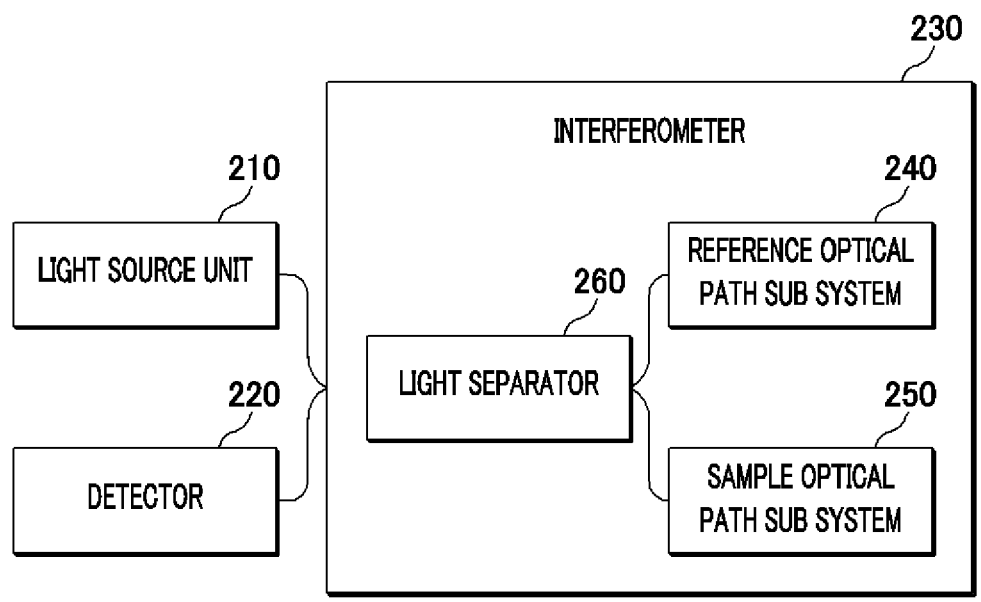
FIG. 3 illustrates the configuration of an optical unit according to an embodiment of the present disclosure.

FIG. 3 illustrates the configuration of an optical unit according to an embodiment of the present disclosure.

Referring to FIG. 3, the optical unit 120 includes a light source unit 210, a detector unit 220 configured to detect the signal generated by a sample (biological tissue) from an optical interference signal of an interferometer 230 and the interferometer 230 configured to cause an optical interference. Here, the interferometer 230 includes a light separator 260 configured to divide a beam of light emitted from the light source unit 210 and send returning beams toward the detector, a reference optical path sub-system 240 configured to allow one of the beams divided by the light separator 260 to be reflected on a reference mirror and resend the reflected beam to the light separator 260 and a sample optical path sub-system 250 configured to allow the other one of the beams divided by the light separator 260 to be incident to the sample (biological tissue) and send returning light to the light separator 260, and the tip end of the sample optical path sub-system 250 is located facing a direction from the optical unit 120 toward a biological tissue to be diagnosed.

As for a conventional OCT device, the sample optical path sub-system 250, together with other elements of light emission assembly, is included in the probe and connected to the light separator 260 through an optical fiber, and the optical fiber is wrapped with a cable (or wire) together with electric wires connected to the circuit unit. Also, the reference optical path sub-system 240 and the sample optical path sub-system 250 can be included in the probe and connected to the light separator 260 through cables, or all of the reference optical path sub-system 240, the sample optical path sub-system 250 and the light separator 260 can be included in the probe and connected to the light source unit 210 and the detector unit 220 through a cable.

However, in the present disclosure, the OCT device needs to be implemented to have a handheld size, and, thus, modules such as a light separator, a reference optical path sub-system, a sample optical path sub-system, a light source unit and a detector unit need to be integrated adjacent to one another in a predetermined area (for example, an area of less than 10 cm). Therefore, optical fibers connecting the respective modules need to be spliced without using connectors, and unnecessary optical fibers, unless they are needed for adjustment of optical power or polarization, need to be removed leaving only a minimum length (less than 10 cm) required for splicing.

Meanwhile, the OCT technology can use the Doppler effect to enable angiography without a contrast agent, and in this case, the phase of the incident light signal serves as a very important factor for angiography. As for the conventional OCT device, if a portion connecting the probe and the main body through a cable (optical fiber) is shaken, the phase of the light signal changes, which lowers the accuracy of angiography. However, according to the present disclosure, the optical fibers connecting the respective components of the optical unit 120 are short in length and fixed inside the device, and, thus, the accuracy of angiography can be improved. Certainly, one may elongate the tip end of the sample optical path sub-system 250 in the light emission assembly using an optical fiber to approach as close as possible to a sample (biological tissue) to be diagnosed (for example, so as to have a predetermined length in such case as laparoscope or endoscope) depending on the shape of the sample.

Further, in an optional embodiment, the components may be in direct contact with each other and the optical fibers may be removed, and small-sized optical components or a geometric optical system may be introduced to achieve miniaturization and cost save of the OCT device 1.

Figure 4:
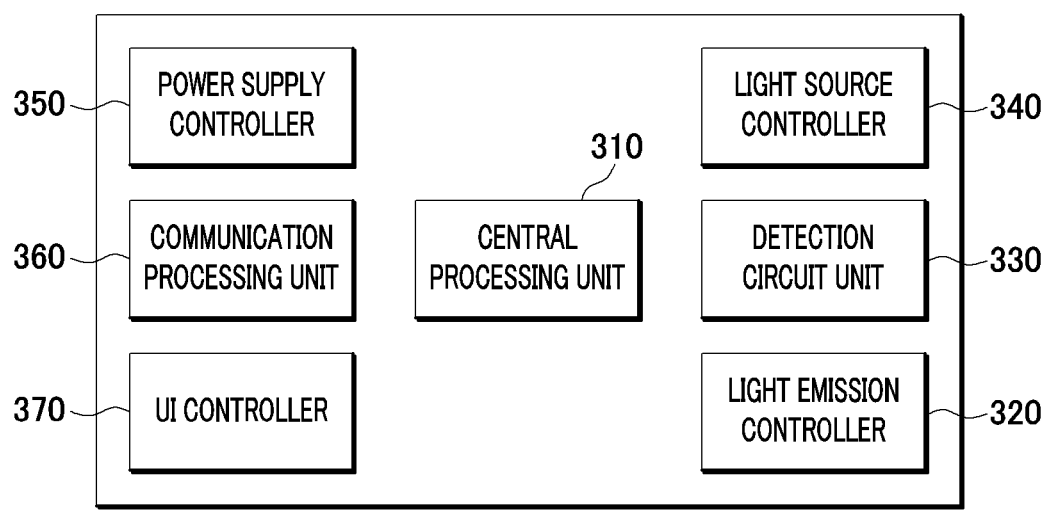
FIG. 4 illustrates the configuration of a circuit unit of the handheld OCT device according to an embodiment of the present disclosure.

FIG. 4 illustrates the configuration of a circuit unit of the handheld OCT device 1 according to an embodiment of the present disclosure.

Referring to FIG. 4, the circuit unit 110 may be configured as electronic circuit boards and provided inside the handheld OCT device 1 and composed of a central processing unit 310, a light emission controller 320, a detection circuit unit 330, a light source controller 340, a power supply controller 350, a communication processing unit 360 and the UI controller unit 370.

First, the light source controller 340 may turn on or off the light source provided in the light source unit 210 or adjust its output level under the control of the central processing unit 310. Also, the light source controller 340 may check the stability of the device while monitoring the temperature around the light source or the output level.

Specifically, the temperature control of the light source unit 210 can be performed using a thermoelectric cooler (TEC) or a simple air cooling method, which can be generally used.

Also, the portion where the light source is mounted is brought into contact with the vicinity of the chip that generates the most heat in order to enhance heat conduction (by using thermal grease if necessary). Further, a rugged surface structure such as a heat dissipation plate may be provided in order to maximize the surface area contacting with air.

Eventually, the light source unit 210 needs to have a structure for effective air flow to dissipate heat inside the device to the outside, and the light source controller 340 needs to monitor whether this process takes place effectively.

The light emission controller 320 may control a beam scanner module configured to change the direction of light emitted from the light emission assembly, or even when additional actuators such as motors are provided, the light emission controller 320 controls the additional actuators. Here, the circuit that controls those actuators is driven with low power consumption, considering the fact that the OCT device 1 is a battery-powered handheld device.

The detection circuit unit 330 converts a light signal into an electrical signal in response to the command from the central processing unit 310 and transmits the electrical signal to the central processing unit 310.

In a handheld or mobile environment, the light source unit 210 needs to perform a low-power operation to reduce power consumption of the battery. For this reason, the detection circuit unit 330 needs to have high sensitivity.

Therefore, in the handheld OCT device 1 of the present disclosure, the optical system needs to be minimized and the detection circuit unit 330 to be coupled to the detector unit 220 needs to be compact in size. Also, the circuit needs to be configured to operate when supplied with power from the battery built in the power supply unit 130.

First, to reduce unnecessary power consumption, the central processing unit 310 controls the power supply controller 350 to switch the device into a standby mode in which the device is stopped when an additional manipulating action is not received from the user or the device is not operated for a predetermined period of time (for example, 1 minute). In this case, current setting parameters before entering the standby mode are backed up in order to immediately continue the operation, which was performed right before the standby mode, when the operation is resumed. To this end, even when the device enters the standby mode, essential components need to be continuously supplied with power in order to maintain the setting parameters.

Here, if the standby mode continues for a predetermined period of time, the central processing unit 310 determines that the user stops using the handheld OCT device 1 and shuts down the handheld OCT device 1.

Also, the central processing unit 310 is configured to control the light source controller 340 to turn on the light source unit 210 for a predetermined warm-up time in advance before a signal to start measurement is received from the UI controller unit 370 through a button or the like and the signal begins to be detected, and automatically turn off the light source of the light source of the light source unit 210 right after the measurement is ended. Through these processes, power consumption can be reduced.

Here, the warm-up time refers to the amount of time required for the output power of the light source to converge into a value within a predetermined range right after the light source turns on.

Further, if the light source controller 340 controls the light source of the light source unit 210 to turn on and warm up, the central processing unit 310 controls the light emission controller 320 to adjust the focus on a measurement site and give a signal for beam scanning.

Here, the central processing unit 310 determines whether or not the device is normal while monitoring the overall state of the handheld OCT device 1. For example, the central processing unit 310 monitors the temperature inside the device in use and controls the cooling fan or the thermoelectric cooler (TEC) to maintain it in an appropriate range. Here, if the time of usage is more than a predetermined amount of time and the temperature increases, which causes a decrease in light output level, a process of applying an additional current to increase the output level to a certain level within an allowable range may be performed.

In contrast, if the temperature increases and the output level is out of the controllable range, a process of sending a warning message to the user or forcibly turning off the light source unit 210 may be performed.

Further, the central processing unit 310 performs signal processing for generating OCT images onto the signal sent from the detection circuit unit 330 and sends/receives signals to/from another device through the communication processing unit 360 or receives a signal input from a button or touch screen through the UI controller unit 370. Furthermore, the central processing unit 310 manages the entire system by indicating operation states through a speaker or an LED indicator or by communicating with the user through the display panel.

The power supply controller 350 is present only in the handheld or mobile OCT device 1 implemented in the present disclosure. Since the entire system is driven by a battery, the power supply controller 350 performs power management through such jobs as shutting down the modules which are not used in the standby mode, switching the system into a sleep mode or automatically shutting down the system if the system is not used for a long time.

The communication processing unit 360 sets a communication channel with respect to a predetermined external device and transmits a control or OCT-related signal to the outside in response to commands from the central processing unit 310 or transmits a signal transmitted from the outside to the central processing unit 310.

For example, when the handheld OCT device 1 shows OCT data in connection with the user terminal, OCT data generated by the handheld OCT device 1 are transmitted to the user terminal through the communication processing unit 360 and the user terminal that has received the OCT data may present the OCT data in real time or later through a display module provided in the user terminal to the user or, after mapping the testee's information previously provided by the user, may store the OCT data. Here, the user terminal may have additional functions for image processing and replay of the OCT data and may manage the information and records of the testee.

The UI controller unit 370 manages input/output of signals to/from UI modules including a button, a touch screen, a speaker, an LED indicator, a display and the like.

In an additional embodiment, a camera having illuminating light may be provided inside the handheld OCT device 1. The camera has the incident beam path shared with the light emission assembly and thus enables real-time acquisition of surface image of a site to be measured and transmits the surface image to the central processing unit 310 and makes it easy to find a measurement site. Further, a co-registration with the OCT signal measured by the detection circuit unit 330 is performed to precisely analyze the measurement site.

Figure 5:
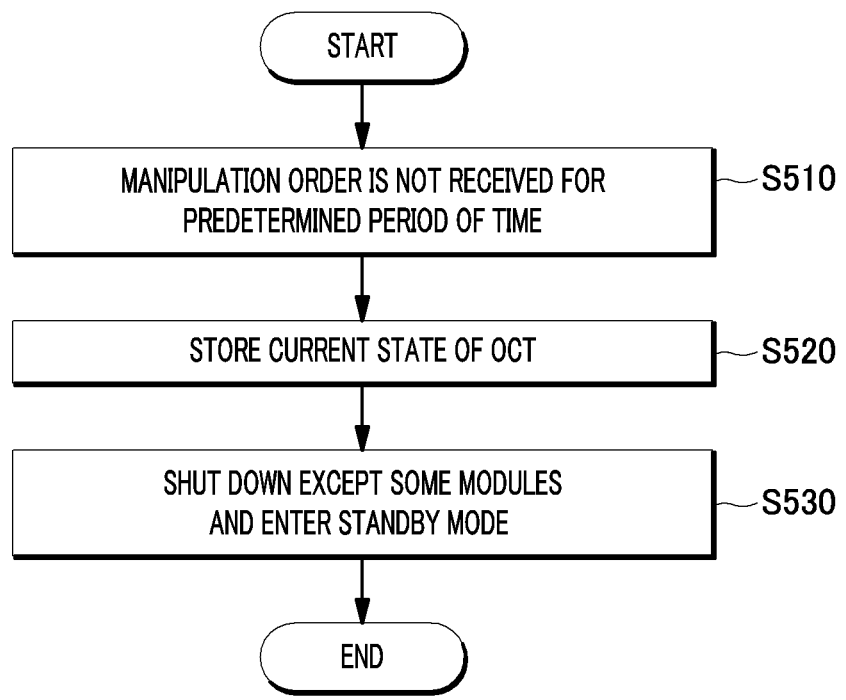
FIG. 5 is a flowchart showing a process of entering a standby mode of the handheld OCT device according to an embodiment of the present disclosure.

FIG. 5 is a flowchart showing a process of entering a standby mode of the handheld OCT device 1 according to an embodiment of the present disclosure.

Referring to FIG. 5, the handheld OCT device 1 enters a standby mode only when any additional manipulation command is not received for a predetermined period of time (S510).

If the handheld OCT device 1 is being operated but the user does not manipulate a manipulation unit for a predetermined period of time, the central processing unit 310 recognizes this and switches the device into a standby mode.

In an additional embodiment, the user may adjust the standby time required to put the device into the standby mode.

After the process S510, the handheld OCT device 1 stores a current state (S520).

This is to immediately recover the handheld OCT device 1 and resume the previous operation when the user manipulates again the handheld OCT device 1 which has entered the standby mode while the user is away.

If the current state is completely stored, the entire device except for some modules is shut down and enters the standby mode (S530).

Here, some modules of the optical unit 120 or the circuit unit 110 are shut down. However, the device is not completely shut down, and, thus, power is continuously supplied to the central processing unit 310 or some modules such as the UI controller unit 370 and the power supply controller 350, in order to respond to a manipulation command from the user at any time.

Further, in an additional embodiment, if the standby mode continues for a predetermined period of time, the circuit unit 110 may determine that the user finishes the operation and completely shut down the handheld OCT device 1.

The above description of the present disclosure is provided for the purpose of illustration, and it would be understood by a person with general knowledge in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. An all-in-one handheld optical coherence tomography (OCT) device, comprising:
   an optical unit provided in a region inside an all-in-one housing;
   a circuit unit provided in another region inside the all-in-one housing and configured to perform signal processing of the optical unit and management of the device; and
   a power supply unit equipped with a built-in battery, configured to supply power to the optical unit and the circuit unit and mounted inside the all-in-one housing,
   wherein a main part of the circuit unit is formed into a planar shape elongated in one direction, and
   a light emission assembly is provided on one side of the all-in-one housing and a light source unit is provided on an other side of the all-in-one housing, wherein the light source unit is configured to supply light through the optical unit, and the light emission assembly is configured to emit the light which has passed through the optical unit, and
   the light source unit is connected to the circuit unit with at least one electric wire, and the circuit unit is located superposed onto the optical unit within an inner space of the all-in-one housing,
   wherein a sample optical path sub-system is provided in a direction from the light emission assembly toward a biological tissue to be examined,
   an interferometer comprising a reference optical path sub-system, the sample optical path sub-system and a light separator, and the reference optical path sub-system, the sample optical path sub-system and the light separator are connected to a detector through a cable while being disposed separately from the detector.

2. The all-in-one handheld OCT device of claim 1, wherein the all-in-one housing has a shape capable of housing the optical unit, the circuit unit and the power supply unit.

3. The all-in-one handheld OCT device of claim 2, wherein optical fibers between the light separator, the reference optical path sub-system, the sample optical path sub-system, the light source and the detector are formed within a predetermined length and connected by splicing without connectors.

4. The all-in-one handheld OCT device of claim 1, wherein a manipulation unit which is connected to the circuit unit and through which the OCT device is manipulated is provided on the outside of the all-in-one housing.

5. The all-in-one handheld OCT device of claim 1, wherein the light source unit, a detector, a reference optical path sub-system, a sample optical path sub-system and a light separator are connected to one another and form the interferometer.

6. The all-in-one handheld OCT device of claim 1, wherein the light emission assembly is elongated to a predetermined length in order to be used as an endoscope or laparoscope.

7. The all-in-one handheld OCT device of claim 1, wherein the circuit unit includes a light source controller, a light emission controller, a detection circuit unit, a central processing unit, a power supply controller, a communication processing unit and a user interface (UI) controller unit.

8. The all-in-one handheld OCT device of claim 7, wherein the central processing unit is configured to control the light source controller to perform ON/OFF control of the light source and adjust an output level of the light source depending on predetermined situations.

9. The all-in-one handheld OCT device of claim 8, wherein the central processing unit is configured to turn on the light source for a predetermined period of warm-up time in advance before initiating a measurement signal, and the central processing unit is configured to automatically turn off the light source after the input of the measurement signal is ended, and
the warm-up time refers to an amount of time required for the output level of the light source to converge into a value within a predetermined range.

10. The all-in-one handheld OCT device of claim 8, the light source controller is configured such that if it receives a signal that a temperature of the light source is higher than a predetermined temperature or a signal that an output level of the light source is lower than a predetermined value, the light source controller adjusts a current to be supplied to the light source.

11. The all-in-one handheld OCT device of claim 10, wherein the light source controller is configured such that if it receives a signal that a temperature of the light source is higher than the predetermined temperature, the light source controller gives a warning alarm or turns off power to the light source.

12. The all-in-one handheld OCT device of claim 7, wherein the light source controller is configured to control the light source to turn on and warm up, and
the light emission controller adjusts focus on a measurement site and gives a signal for beam scanning.

13. The all-in-one handheld OCT device of claim 7, wherein the light source controller of the circuit unit and the light source unit including the light source of the optical unit have a rugged surface structure in order to enhance heat conduction of internal chips.

14. The all-in-one handheld OCT device of claim 1,
wherein if the OCT device is not operated for a predetermined period of time, the OCT device is configured to be put into a standby mode in which the OCT device is paused, and
wherein the circuit unit is configured to back up parameters set while a user has used the OCT right before standby mode, in order for the OCT device to respond to the user's manipulation.

15. The all-in-one handheld OCT device of claim 14,
wherein if the OCT device is maintained in the standby mode for a predetermined period of time, a power supply controller is configured to put the OCT device into a mode in which the OCT device is shut down.

* * * * *